United States Patent
Suzuki et al.

(10) Patent No.: US 8,176,618 B2
(45) Date of Patent: May 15, 2012

(54) METHOD FOR PRODUCING GAS SENSOR

(75) Inventors: Yoshio Suzuki, Nagoya (JP); Kouji Tagawa, Nagoya (JP); Kunihiko Nakagaki, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 487 days.

(21) Appl. No.: 12/036,393

(22) Filed: Feb. 25, 2008

(65) Prior Publication Data

US 2008/0202205 A1 Aug. 28, 2008

(30) Foreign Application Priority Data

Feb. 27, 2007 (JP) ................................. 2007-047409

(51) Int. Cl.
*G01R 3/00* (2006.01)
(52) U.S. Cl. .......... 29/595; 29/594; 29/609.1; 73/23.21; 73/866.5; 83/351; 83/353
(58) Field of Classification Search .................. 29/592.1, 29/594, 609; 73/23.21, 866.5; 72/464; 83/351, 83/353
See application file for complete search history.

(56) References Cited

U.S. PATENT DOCUMENTS

| | | | |
|---|---|---|---|
| 4,450,065 A | | 5/1984 | Yamada et al. |
| 4,722,778 A | | 2/1988 | Hayakawa |
| 4,732,663 A | | 3/1988 | Kato et al. |
| 4,919,689 A | * | 4/1990 | Pyzik et al. .................. 51/309 |
| 5,021,372 A | * | 6/1991 | Pyzik et al. .................. 501/95.3 |
| 5,031,445 A | | 7/1991 | Kato et al. |
| 5,118,645 A | * | 6/1992 | Pyzik et al. .................. 501/98.1 |
| 5,144,249 A | | 9/1992 | Kurishita et al. |
| 6,645,360 B1 | | 11/2003 | Eisele et al. |
| 6,939,607 B2 | * | 9/2005 | Kato et al. .................. 428/336 |
| 7,160,422 B2 | | 1/2007 | Imamura et al. |
| 2004/0158971 A1 | | 8/2004 | Kawashima |
| 2005/0211554 A1 | | 9/2005 | Kurachi et al. |

FOREIGN PATENT DOCUMENTS

| | | |
|---|---|---|
| DE | 198 15 174 A1 | 10/1999 |
| JP | 58-153155 A1 | 9/1983 |
| JP | 59156922 A * | 9/1984 |
| JP | 61-097562 A1 | 5/1986 |
| JP | 01-281858 A1 | 11/1989 |
| JP | 05169537 A * | 7/1993 |
| JP | 2786507 B2 | 5/1998 |
| JP | 2000-005992 A1 | 1/2000 |
| JP | 2004-003963 A1 | 1/2004 |
| JP | 2006-201191 A1 | 8/2006 |
| WO | 93/15864 A1 | 8/1993 |

OTHER PUBLICATIONS

U.S. Appl. No. 12/036,383, filed Feb. 25, 2008, Suzuki et al.
U.S. Final Office Action dated Jan. 31, 2012 for co-pending U.S. Appl. No. 12/036,383.

* cited by examiner

*Primary Examiner* — Paul D Kim
(74) *Attorney, Agent, or Firm* — Burr & Brown

(57) ABSTRACT

A solid electrolyte body is placed on and fixed to an upper plate of a press jig such that a major surface (an upper surface) of the solid electrolyte body faces one major surface of a guide plate having an open space. The upper plate is rotated by a transfer mechanism to incline the solid electrolyte body in one direction, and the inclined solid electrolyte body is moved toward the other major surface of the guide plate such that a first edge of the solid electrolyte body protrudes from the open space. Then, a cutter is slid along the other major surface, so that the first edge is chamfered to form a first chamfered portion.

3 Claims, 16 Drawing Sheets

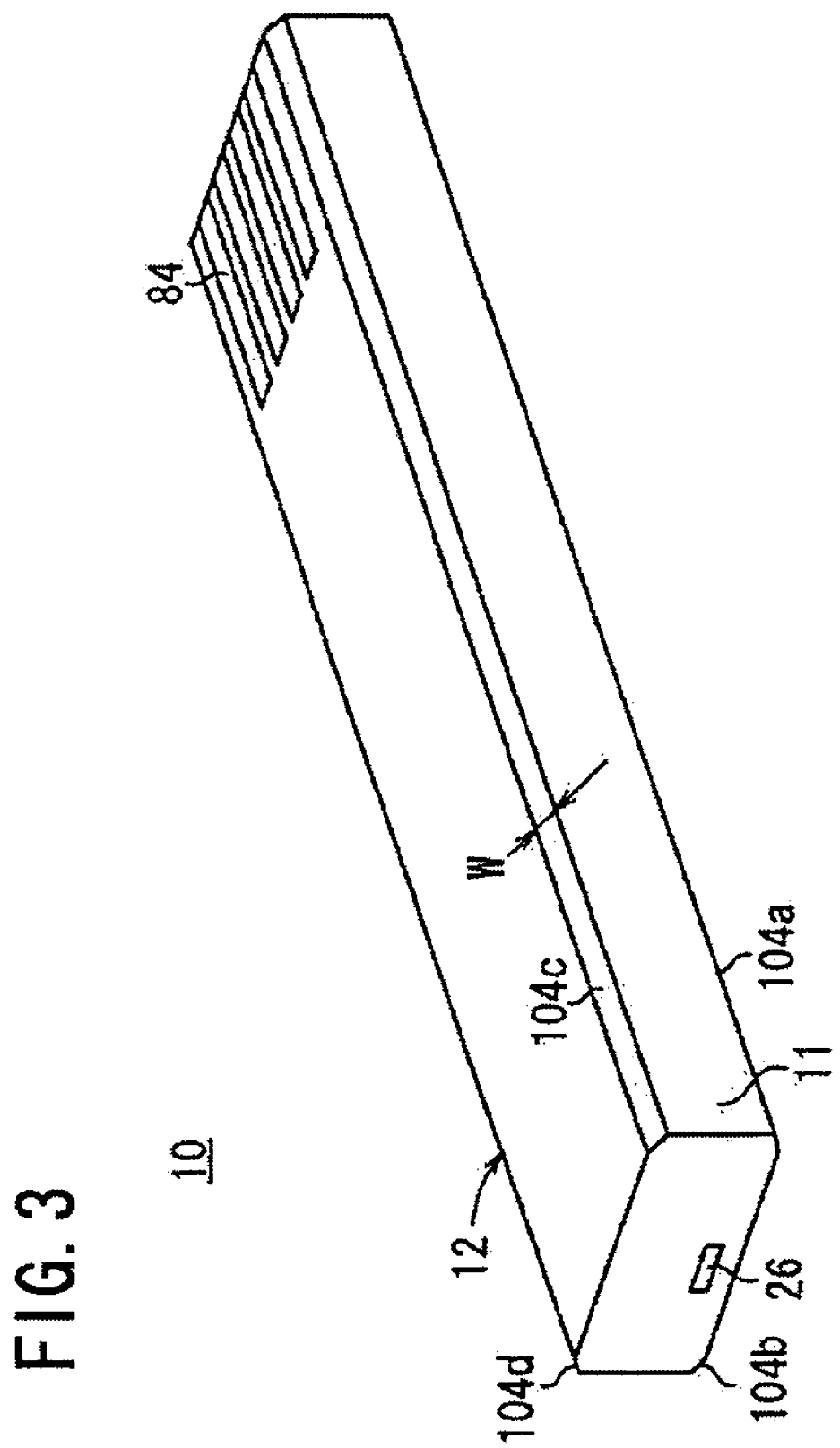

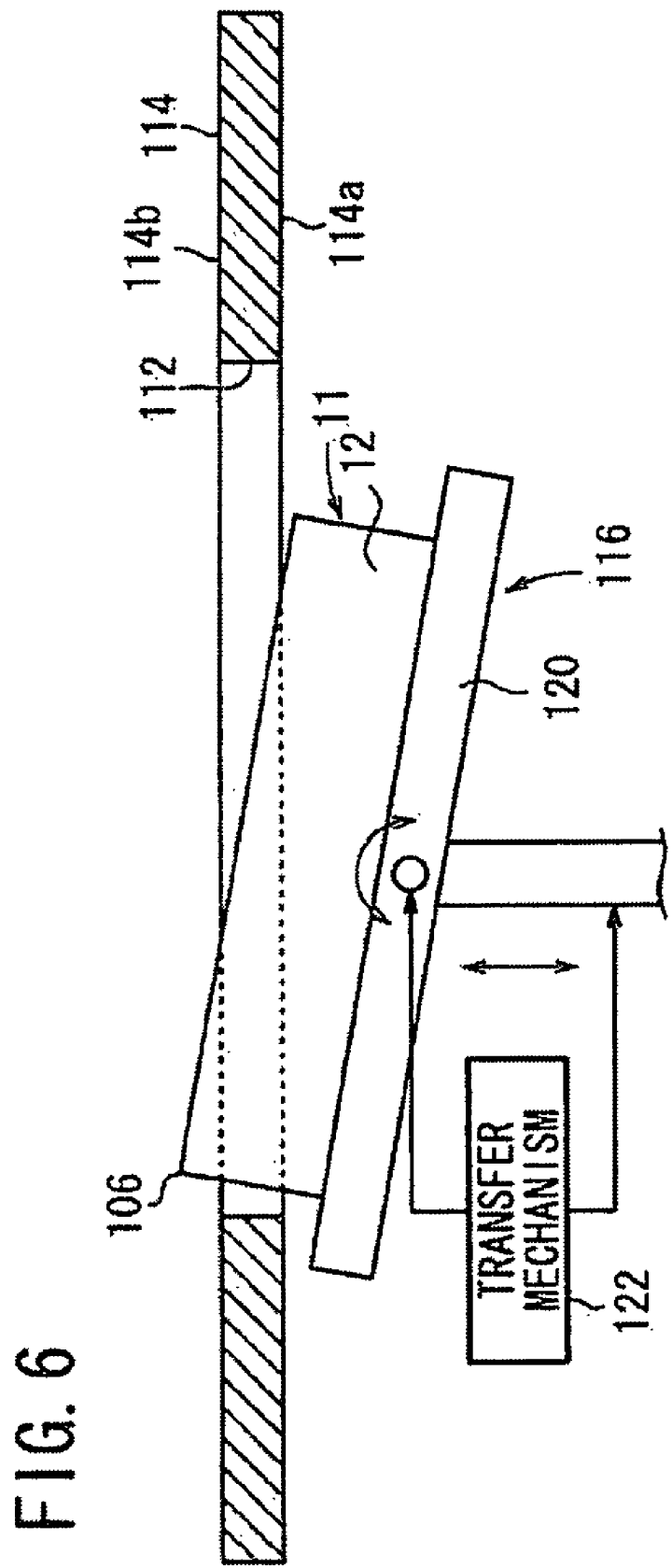

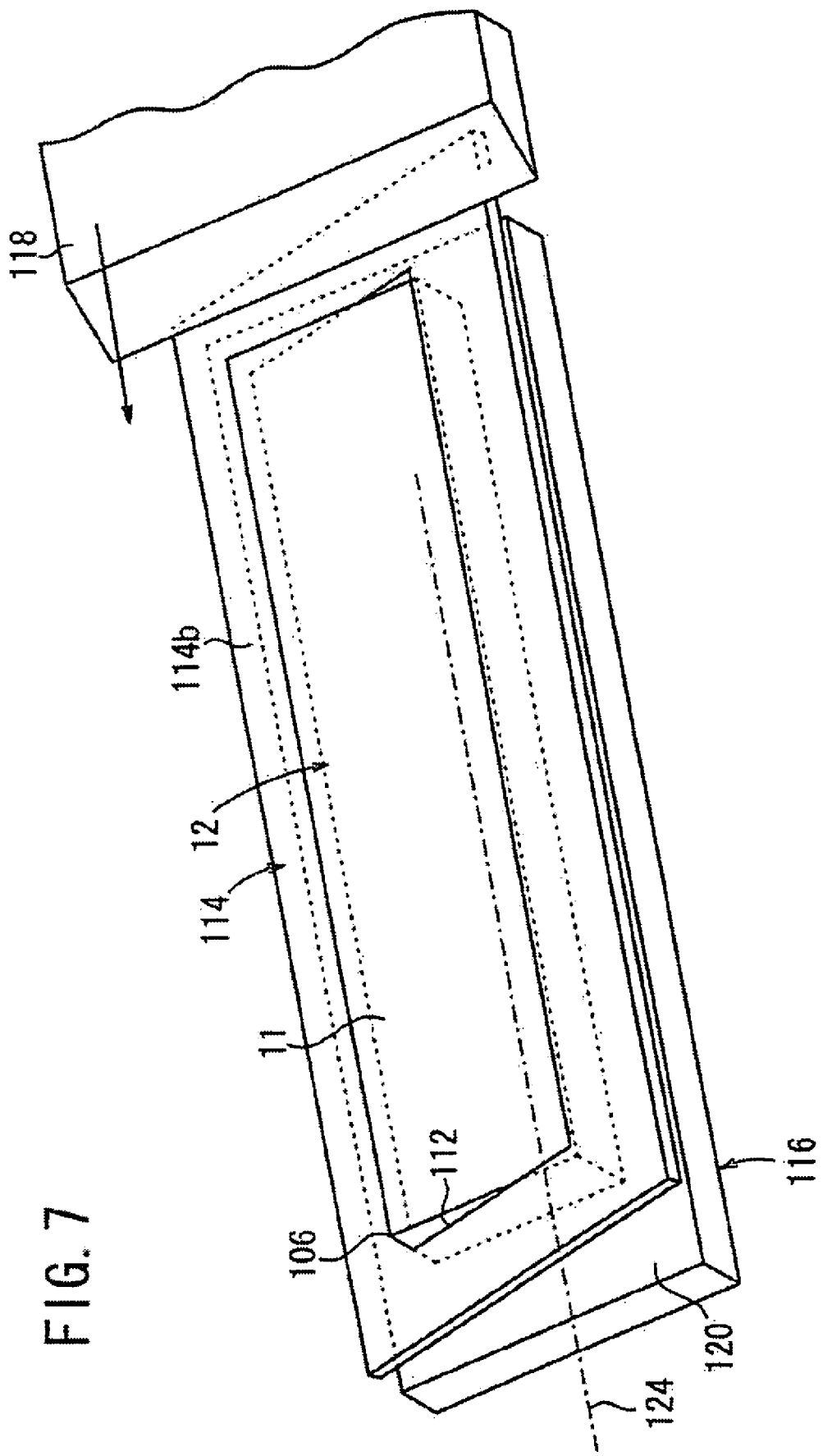

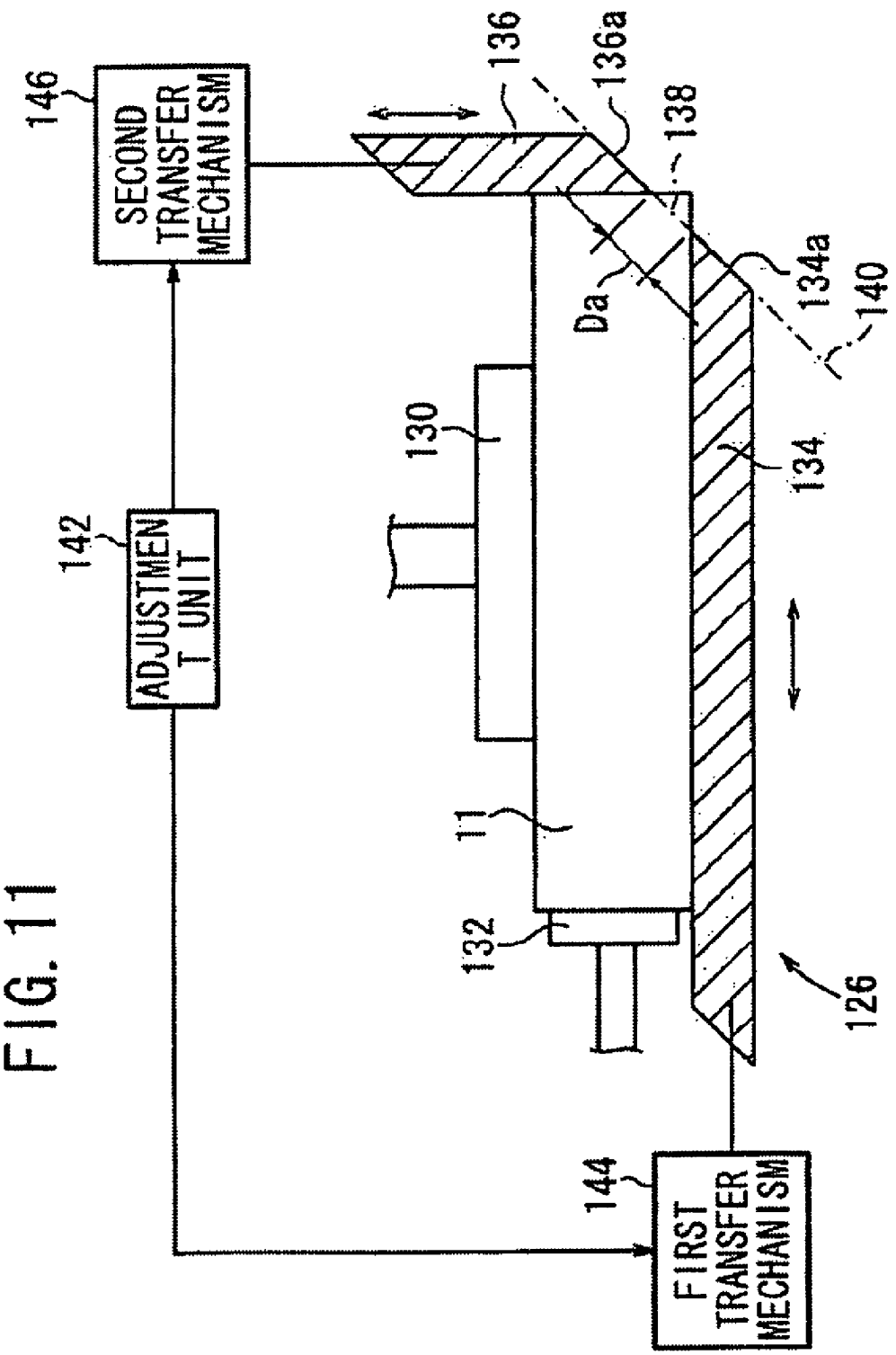

METHOD FOR PRODUCING GAS SENSOR

CROSS-REFERENCE TO RELATED APPLICATIONS

This application is based upon and claims the benefit of priority from Patent Application No. 2007-047409 filed on Feb. 27, 2007 in the Japanese Patent Office, of which the contents are incorporated herein by reference.

BACKGROUND OF THE INVENTION

1. Field of the Invention

The present invention relates to a method for producing a gas sensor comprising a sensor element for detecting the concentration of a specific gas component in a measurement gas, which has a rectangular solid structure of a solid electrolyte body containing a ceramic material.

2. Description of the Related Art

Among gas sensors, certain oxygen sensors have been known as an oxygen concentration detector. The oxygen sensors are used for detecting the oxygen concentration of an exhaust gas from an internal combustion engine, thereby optimally controlling the combustion state of the engine based on the detected signals, to achieve exhaust gas cleaning, fuel cost reduction, etc.

In one of such oxygen sensors, an oxygen ion-conductive solid electrolyte, such as zirconium oxide doped with calcium oxide, yttrium oxide, or the like, is used for a partition wall. Electrodes are formed on the surfaces of the partition wall to provide a sensor element. One of the electrodes is exposed to a reference atmosphere, the other is exposed to a measurement gas such as an exhaust gas, and an electromotive force generated based on the theory of oxygen concentration cell is obtained as a detection signal.

Among oxygen sensor elements, long plate elements, which have at one end an oxygen-detecting section to be exposed to a measurement gas such as an exhaust gas, have recently attracted much attention instead of bottomed cylinder elements. Such long plate elements can be produced and miniaturized easily. Examples of the plate elements are described in Japanese Laid-Open Patent Publication Nos. 58-153155 and 61-097562, etc.

In another oxygen sensor, an oxide such as titanium oxide is disposed on a long plate substrate to provide a sensor element, the electrical resistance of the oxide changing depending on oxygen concentration. The sensor element is exposed to a measurement gas such as an exhaust gas to detect the electrical resistance change depending on the oxygen partial pressure.

In the oxygen sensors, an oxygen-detecting section of an oxygen sensor element is exposed to a measurement gas such as an exhaust gas with high temperature, and the oxygen-detecting section is maintained in some cases at high temperature by a heater built in the oxygen sensor element to achieve sufficient oxygen-detecting function. Thus, the sensor element is subjected to thermal stress. When the sensor element is plate-shaped, the stress is concentrated at the edges, so that the element is often cracked to deteriorate its oxygen concentration-detecting function.

For example, in an oxygen sensor element disclosed in Japanese Patent No. 2786507, edge portions at the end of a plate substrate are chamfered, whereby the stress concentration is relaxed to improve the thermal shock resistance.

SUMMARY OF THE INVENTION

An object of the present invention is to provide a method for producing a gas sensor, capable of easily controlling a chamfering process, thereby easily producing a high-performance gas sensor excellent in thermal shock resistance such as the above gas sensor of Japanese Patent No. 2786507.

The first method of the present invention is used for producing a gas sensor comprising a sensor element for detecting the concentration of a particular gas component in a measurement gas, the sensor element having a rectangular solid structure of a solid electrolyte body containing a ceramic material. The first method comprises the first step of placing the solid electrolyte body such that a surface of the solid electrolyte body faces one major surface of a guide plate having a through-hole, into which an edge of the solid electrolyte body is inserted, the second step of inclining the solid electrolyte body in a direction, and moving the solid electrolyte body toward the other major surface of the guide plate such that an edge of the solid electrolyte body protrudes from the through-hole, and the third step of sliding a cutter along the other major surface to chamfer the edge.

By using the first method, a high-performance gas sensor such as the above gas sensor of Japanese Patent No. 2786507 can be easily produced, and the chamfering process can be easily carried out. The width of the resultant chamfered portion can be controlled by changing the angle of the inclination of the solid electrolyte body, thereby changing the extent of the protrusion of the solid electrolyte body.

The first method of the present invention may further comprise the fourth step of inclining the solid electrolyte body in the opposite direction, and moving the solid electrolyte body toward the other major surface of the guide plate such that another edge of the solid electrolyte body protrudes from the through-hole, and the fifth step of sliding the cutter along the other major surface to chamfer the another edge.

Further, in the first method of the present invention, after the fifth step, the solid electrolyte body may be placed such that the opposite surface of the solid electrolyte body faces the one major surface of the guide plate, and the second to fifth steps may be carried out again to consequently chamfer four edges of the solid electrolyte body.

The second method of the present invention is used for producing a gas sensor comprising a sensor element for detecting the concentration of a particular gas component in a measurement gas, the sensor element having a rectangular solid structure of a solid electrolyte body containing a ceramic material. A positioning jig used in the second method comprises a first plate, a second plate nonparallel to the first plate, and a space formed between the first and second plates, and an end surface of the first plate is located in the vicinity of an end surface of the second plate. The second method comprises the first step of placing the solid electrolyte body such that a major surface of the solid electrolyte body is in contact with the first plate, a side surface thereof is in contact with the second plate, and an edge between the major surface and the side surface protrudes from the space, and the second step of sliding a cutter in the longitudinal direction of the edge protruding from the space to chamfer the edge.

By using the second method, a high-performance gas sensor such as the above gas sensor of Japanese Patent No. 2786507 can be easily produced, and the chamfering process can be easily carried out. The width of the resultant chamfered portion can be controlled by changing the distance between the first and second plates, thereby changing the width of the space.

In the second method of the present invention, the end surface of the first plate, the space, and the end surface of the second plate may form a surface in the positioning jig, and the cutter may be slid along the surface to chamfer the edge in the second step. In this case, the edge protruding from the space between the first and second plates can be smoothly chamfered by the cutter.

In the second method of the present invention, the first and second steps may be carried out repeatedly to chamfer four edges of the solid electrolyte body.

As described above, by using the method of the present invention, a high-performance gas sensor such as the above gas sensor of Japanese Patent No. 2786507 can be easily produced, and the chamfering process can be easily carried out.

The above and other objects, features and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 3 is a perspective view showing the shape of a solid electrolyte body in a sensor element of the gas sensor;

FIG. 6 is a structural view showing an apparatus for a first producing method;

FIG. 7 is a perspective view showing the apparatus for the first producing method, particularly an upper plate having a solid electrolyte body, a guide plate, and a cutter;

FIG. 11 is a structural view showing an apparatus for a second producing method;

DETAILED DESCRIPTION OF THE INVENTION

An illustrative embodiment of the method of the present invention for producing a gas sensor will be described below with reference to FIGS. 1 to 16C.

A gas sensor 10, which can be produced by the method of this embodiment, will be described below with reference to FIGS. 1 to 5D.

Figure 1:
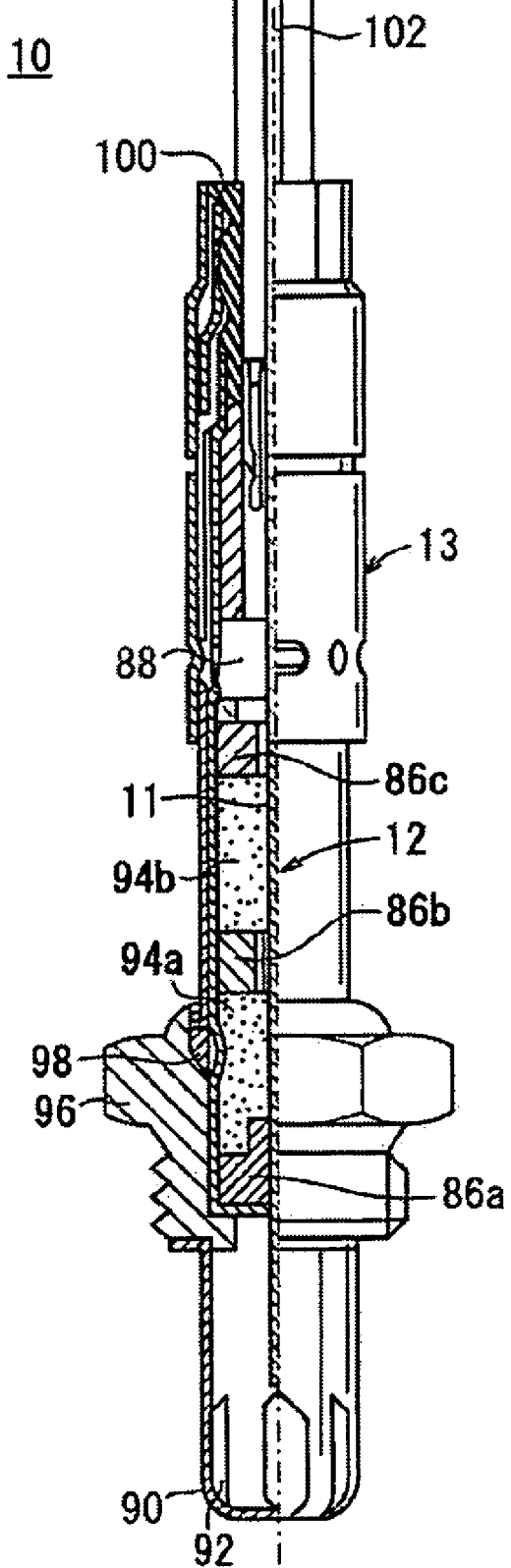
FIG. 1 is a partially broken side view showing a gas sensor produced by a method according to an embodiment of the present invention.

As shown in FIG. 1, the gas sensor 10 has a sensor element 12 for detecting the concentration of a particular gas component in a measurement gas and a cylindrical metal housing 13 for supporting the sensor element 12 inside. The sensor element 12 has a rectangular solid structure containing an oxygen ion-conductive, solid electrolyte body 11 of a porcelain zirconia ($ZrO_2$), etc.

Figure 2:
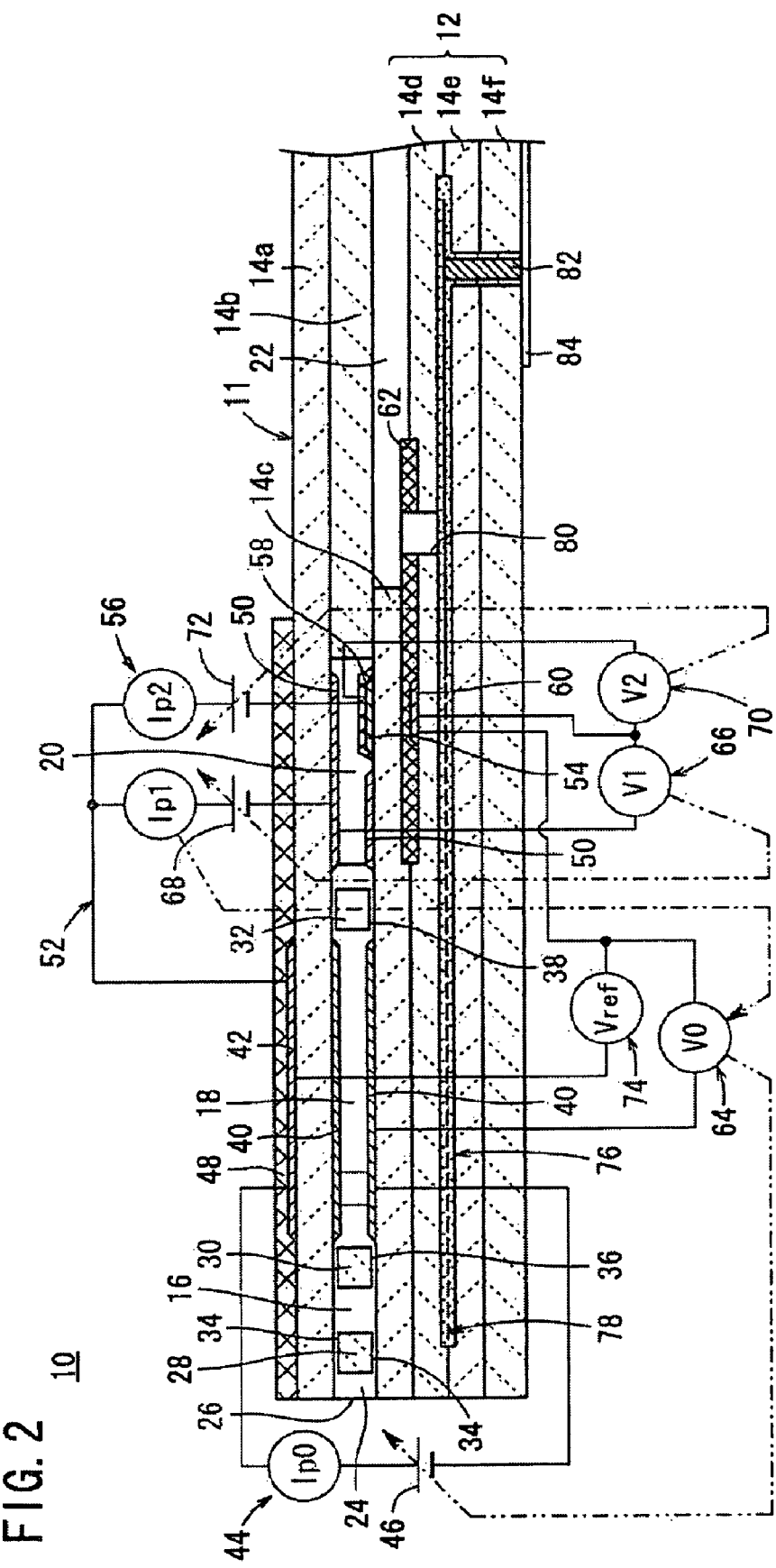
FIG. 2 is a cross-sectional view showing the inner structure of the gas sensor.

As shown in FIG. 2, the sensor element 12 has an integral plate-shaped structure containing a stack of a plurality of dense, airtight, oxygen ion-conductive, solid electrolyte layers (e.g., first to sixth solid electrolyte layers 14a to 14f). Each of the first to sixth solid electrolyte layers 14a to 14f contains a known oxygen ion-conductive solid electrolyte material such as porcelain zirconia ($ZrO_2$). The integral sensor element 12 can be easily formed by a known process of burning a stack of unburned solid electrolyte layers to integrate the layers.

At least four internal spaces (a first internal space 16, a second internal space 18, a third internal space 20, and a fourth internal space 22) are formed in the sensor element 12.

The first to third internal spaces 16, 18, 20 are formed between the first solid electrolyte layer 14a positioned uppermost in FIG. 2 and the third solid electrolyte layer 14c positioned at the third from the top such that the first and third solid electrolyte layers 14a, 14c are stacked and integrated with a spacer of the second solid electrolyte layer 14b in-between.

The first to third internal spaces 16, 18, 20 have heights corresponding to the thickness of the second solid electrolyte layer 14b, and extend in the longitudinal direction of the sensor element 12 between the first and third solid electrolyte layers 14a, 14c as spaces without the second solid electrolyte layer 14b.

Thus, the first to third internal spaces 16, 18, 20, respectively, have rectangular shapes when viewed from the above, are separated from each other, and extend in the longitudinal direction of the sensor element 12 into certain widths, in series.

Among the first to third internal spaces 16, 18, 20, the first internal space 16 is closest to a gas inlet 26 to be hereinafter described, and acts as a buffer space for buffering rapid oxygen concentration change by external pulsation of an exhaust gas. The second internal space 18 acts as a control space for controlling the oxygen partial pressure of the measurement gas, and the third internal space 20 acts as a measurement space for fine-controlling the oxygen partial pressure of the measurement gas and measuring an oxide such as a nitrogen oxide (NOx) in the gas.

The fourth internal space 22 is separated from the first to third internal spaces 16, 18, and 20, and extends in the longitudinal direction of the sensor element 12 between the second and fourth solid electrolyte layers 14b, 14d as a space without the third solid electrolyte layer 14c. The fourth internal space 22 acts as a reference gas inlet path for introducing a reference gas into the sensor element 12, and the path is opened at the proximal end of the sensor element 12 to atmospheric air.

Thus, in the following description, the first internal space 16 is referred to as the buffer space 16, the second internal space 18 is referred to as the control space 18, the third internal space 20 is referred to as the measurement space 20, and the fourth internal space 22 is referred to as the reference gas inlet path 22.

A clogging-preventive space 24 opening outward is formed between the first and third solid electrolyte layers 14a, 14c at the outer side of the buffer space 16, i.e. the distal end side of the sensor element 12. The opening of the clogging-preventive space 24 acts as the gas inlet 26 for introducing the external measurement gas into the sensor element 12.

The clogging-preventive space 24 is separated from the buffer space 16 by a first partition wall 28 of the second solid electrolyte layer 14b, the buffer space 16 is separated from the control space 18 by a second partition wall 30 of the second solid electrolyte layer 14b, and the control space 18 is separated from the measurement space 20 by a third partition wall 32 of the second solid electrolyte layer 14b.

First slits 34 are formed on the upper and lower surfaces of the first partition wall 28 (between the first partition wall 28 and the first solid electrolyte layer 14a, and between the first partition wall 28 and the third solid electrolyte layer 14c), respectively. The first slits 34 act as a first diffusion rate-determining means for the measurement gas. The external measurement gas is introduced from the gas inlet 26 through the clogging-preventive space 24 to the buffer space 16 under a predetermined diffusion resistance of the first slits 34.

Second slits 36 are formed on the upper and lower surfaces of the second partition wall 30 for separating the buffer space 16 and the control space 18 (between the second partition wall 30 and the first solid electrolyte layer 14a, and between the second partition wall 30 and the third solid electrolyte layer 14c), respectively. The second slits 36 act as a second diffusion rate-determining means for the measurement gas. The measurement gas in the buffer space 16 is introduced to the control space 18 under a predetermined diffusion resistance of the second slits 36.

Third slits 38 are formed on the upper and lower surfaces of the third partition wall 32 for separating the control space 18 and the measurement space 20 (between the third partition wall 32 and the first solid electrolyte layer 14a, and between the third partition wall 32 and the third solid electrolyte layer 14c), respectively. The third slits 38 act as a third diffusion rate-determining means for the measurement gas. The measurement gas having a controlled oxygen concentration (partial pressure) in the control space 18 is introduced to the measurement space 20 under a predetermined diffusion resistance of the third slits 38.

In the gas sensor 10 of this embodiment, an inner pumping electrode 40 containing a porous cermet is formed on the inner wall of the control space 18, and an outer pumping electrode 42 is formed in a portion corresponding to the inner pumping electrode 40 on the upper surface of the first solid electrolyte layer 14a. The inner pumping electrode 40, the outer pumping electrode 42, and the first to third solid electrolyte layers 14a to 14c form an electrochemical pumping cell, i.e. a main pumping cell 44.

In the main pumping cell 44, a desired control voltage (pumping voltage) Vp1 is applied between the inner pumping electrode 40 and the outer pumping electrode 42 by an external first variable power source 46, so that a pumping current Ip0 flows between the inner pumping electrode 40 and the outer pumping electrode 42 in the positive or negative direction. Thus, oxygen in the control space 18 is pumped to the outside, or alternatively external oxygen is pumped into the control space 18, to control the oxygen concentration (partial pressure) in the control space 18.

The buffer space 16, the first partition wall 28, the second partition wall 30, the first slits 34, and the second slits 36 provide the following effect.

In general, oxygen is rapidly introduced from a gas inlet into an internal space of a sensor element due to pulsation of an external exhaust gas. However, in this embodiment, the external oxygen is not introduced directly into the internal space (processing space), and the oxygen is introduced through the first slits 34 into the buffer space 16 and further introduced through the second slits 36 into the control space 18. Therefore, the rapid oxygen concentration change by exhaust gas pulsation can be counteracted by the buffer space 16, the first slits 34, and the second slits 36, whereby the influence of the pulsation on the control space 18 is substantially negligible small. As a result, the correlation is improved between the oxygen pumping amount in the control space 18 of the main pumping cell 44 and the oxygen concentration of the measurement gas, so that the measurement accuracy can be improved, and the control space 18 can be used also as a sensor for detecting air-fuel ratio, etc. To obtain the effect advantageously, each of the first and second slits 34 and 36 formed on the first and second partition walls 28 and 30 preferably has a width of 10 μm or less.

By forming the clogging-preventive space 24 opening outward at the distal end of the sensor element 12, the inlets of the buffer space 16 can be prevented from clogging with particles of soot, oil combustion waste, or the like in the external measurement gas introduced through the gas inlet 26. As a result, a NOx component can be measured with higher accuracy.

The inner pumping electrode 40 and the outer pumping electrode 42 in the main pumping cell 44 generally contain a porous cermet, for example, composed of a metal such as Pt and a ceramic material such as $ZrO_2$. The inner pumping electrode 40 is placed in the control space 18 and brought into contact with the measurement gas, and thereby should be composed of a material that causes no changes of the NOx component in the measurement gas, i.e. a material having a low or no decomposing/reducing ability for the NOx component such as NO or $NO_2$. For example, the inner pumping electrode 40 may contain a perovskite compound ($La_3CuO_4$, etc.), a cermet of a ceramic material and a metal having a low catalytic activity (Au, etc.), or a cermet of a ceramic material, a Pt group metal, and a metal having a low catalytic activity (Au, etc.) In this embodiment, the outer pumping electrode 42 is covered with a porous protecting layer 48 containing alumina, etc., whereby the outer pumping electrode 42 is protected while preventing adhesion of an oil component, etc. contained in the external measurement gas.

An auxiliary pumping electrode 50 containing a porous cermet is formed on the inner wall of the measurement space 20. Thus, the auxiliary pumping electrode 50, an appropriate electrode on the outer surface of the sensor element 12 (the outer pumping electrode 42, etc.), and the first to third solid electrolyte layers 14a to 14c form an auxiliary electrochemical pumping cell, i.e. an auxiliary pumping cell 52, to control the oxygen concentration (partial pressure) in the measurement space 20.

The auxiliary pumping electrode 50 is composed of a material having a low or no decomposing/reducing ability for the NOx component in the measurement gas, like the inner pumping electrode 40 in the main pumping cell 44. For example, the auxiliary pumping electrode 50 may contain a porous cermet composed of Pt (platinum) and $ZrO_2$ with 1% of Au (gold).

In this embodiment, a detecting electrode 54 is formed in the measurement space 20. The detecting electrode 54, the outer pumping electrode 42, the first to third solid electrolyte layers 14a to 14c form an electrochemical pumping cell, i.e. a measuring pumping cell 56, whereby oxygen generated by decomposition of nitrogen oxide (NOx) around the detecting electrode 54 is pumped out and the amount of the oxygen is detected.

As shown in FIG. 2, the detecting electrode 54 is covered with an electrode-protecting layer 58 of a porous ceramic containing alumina in the measurement space 20. Thus, the detecting electrode 54 can be protected while preventing adhesion of an inert component such as a metal, etc. emitted from the auxiliary pumping electrode 50 in the measurement space 20, and the catalytic activity (the NOx-decomposing/reducing ability) of the detecting electrode 54 can be efficiently maintained.

In the sensor element 12, a reference electrode 60, which can be in contact with a reference gas in the reference gas inlet path 22, is formed on the side opposite to the measurement space side on the third solid electrolyte layer 14c.

The reference electrode 60 is formed on a sealing layer of the fourth solid electrolyte layer 14d, and is covered with a porous alumina layer 62 for introducing air. The reference gas in the reference gas inlet path 22 is brought through the porous alumina layer 62 into contact with the reference electrode 60.

By using the reference electrode 60, the oxygen concentration (partial pressure) in the control space 18 or the measurement space 20 can be measured.

Thus, in this embodiment, the inner pumping electrode 40 in the main pumping cell 44, the reference electrode 60, and the first to fourth solid electrolyte layers 14a to 14d form a first oxygen partial pressure-detecting cell 64 for controlling the main pumping cell 44, to detect the oxygen concentration (partial pressure) in the control space 18.

Further, the auxiliary pumping electrode 50 in the auxiliary pumping cell 52, the reference electrode 60, and the first to fourth solid electrolyte layers 14a to 14d form a second oxygen partial pressure-detecting cell 66 for controlling the auxiliary pumping cell 52, to detect the oxygen partial pressure in the measurement space 20. The voltage of a second variable power source 68 is controlled by the second oxygen partial pressure-detecting cell 66. The second variable power source 68 is used for operating the auxiliary pumping cell 52, and its pumping current Ip1 is used for controlling an electromotive force V0 in the first oxygen partial pressure-detecting cell 64.

Further, the detecting electrode 54, the reference electrode 60, and the first to fourth solid electrolyte layers 14a to 14d form a third oxygen partial pressure-detecting cell 70, to detect the oxygen partial pressure around the detecting electrode 54.

A third variable power source 72 is controlled based on an electromotive force V2 detected in the third oxygen partial pressure-detecting cell 70. The third variable power source 72 is used for operating the measuring pumping cell 56, to obtain a pumping current Ip2 corresponding to the nitrogen oxide concentration of the measurement gas.

The outer pumping electrode 42, the reference electrode 60, and the first to fourth solid electrolyte layers 14a to 14d form an electrochemical sensor cell 74. The oxygen partial pressure (concentration) of the external measurement gas can be detected based on an electromotive force Vref obtained by the sensor cell 74.

As shown in FIG. 2, in the sensor element 12, a plurality of ceramic layers, i.e. the fourth to sixth solid electrolyte layers 14d to 14f are stacked and integrated on the side of the third solid electrolyte layer 14c opposite to the side having the internal spaces (16, 18, 20). A heater layer 76, which generates heat under a power from an external source, is vertically interposed between the adjacent fourth and fifth solid electrolyte layers 14d, 14e.

The heater layer 76 is used for heating the first to sixth solid electrolyte layers 14a to 14f in the sensor element 12 at a predetermined temperature to increase the oxygen ion conductivity thereof. A heater element 78 is vertically interposed between electric insulating layers composed of alumina, etc., whereby the heater element 78 is electrically insulated from the fourth and fifth solid electrolyte layers 14d, 14e. A pressure diffusion hole 80 passes through the fourth solid electrolyte layer 14d in the proximal side of the sensor element 12, and the heater layer 76 is communicated by the pressure diffusion hole 80 to the reference gas inlet path 22, to relax an increased inner pressure in the heater layer 76. Further, the heater element 78 in the heater layer 76 is communicated with the surface of the sensor electrode via an insulated through-hole 82 penetrating through the fifth and sixth solid electrolyte layers 14e, 14f, and connected to one of connector pads 84 insulated from the sixth solid electrolyte layer 14f. The heater element 78 in the heater layer 76 heats at least the first to third solid electrolyte layers 14a to 14c separating the control space 18 and the measurement space 20 at a predetermined temperature.

The nitrogen oxide (NOx) concentration of the measurement gas is detected by the gas sensor 10 of this embodiment as follows. First, the external measurement gas is introduced from the clogging-preventive space 24 at the distal end of the sensor element 12 through the first slits 34 formed on the upper and lower surfaces of the first partition wall 28 into the buffer space 16, and is further introduced through the second slits 36 formed on the upper and lower surfaces of the second partition wall 30 into the control space 18. Then, the voltage of the first variable power source 46 is controlled, whereby the pumping current Ip0 of the main pumping cell 44 is controlled, to stabilize the electromotive force V0 in the first oxygen partial pressure-detecting cell 64. In this process, the oxygen partial pressure in the control space 18 is adjusted at a predetermined value, e.g. about $10^{-7}$ atm.

The measurement gas is introduced from the control space 18 through the third slits 38 formed on the upper and lower surfaces of the third partition wall 32 into the measurement space 20. The voltage of the second variable power source 68 is controlled based on an electromotive force V1 detected by the second oxygen partial pressure-detecting cell 66, and an oxygen pumping operation is carried out by the auxiliary pumping cell 52 under a power from the second variable power source 68, so that the oxygen partial pressure in the measurement space 20 is reduced to the extent that the oxygen has substantially no effect on the NOx measurement. The pumping current Ip1 of the auxiliary pumping cell 52 is input as a control signal into the first oxygen partial pressure-detecting cell 64 to control its electromotive force V0, whereby the gradient of the oxygen partial pressure is stabilized in the measurement space 20 over the third slits 38 and the auxiliary pumping electrode 50.

Further, the gas having the oxygen partial pressure controlled in the measurement space 20 is introduced through the electrode-protecting layer 58 to the detecting electrode 54 under a predetermined diffusion resistance. The NOx in the gas is reduced or decomposed around the detecting electrode 54 to produce oxygen.

Thus produced oxygen is pumped by the measuring pumping cell 56. In this step, the voltage of the third variable power source 72 is controlled to stabilize the electromotive force V2 in the third oxygen partial pressure-detecting cell 70. The amount of the oxygen produced around the detecting electrode 54 is proportional to the NOx concentration of the measurement gas, and thus the NOx concentration can be calculated using the pumping current Ip2 in the measuring pumping cell 56.

Lead wires from the above electrodes and heater are introduced outside, and are electrically connected to corresponding connector pads 84, respectively, as shown in FIG. 3.

The housing 13 shown in FIG. 1 contains three ceramic supporting members (first to third supporting members 86a to 86c) for supporting longitudinal intermediate portions of the sensor element 12, and a connector 88 for supporting the rear end of the sensor element 12 and for electrically connecting the connector pad 84 formed on the solid electrolyte body 11 to the outside. A protective cover 90 is attached to the distal end of the housing 13. An inlet hole 92 for introducing the measurement gas into the housing 13 is formed on the protective cover 90.

A space between the first and second supporting members 86a, 86b is filled with a first talc 94a, a space between the second and third supporting members 86b, 86c is filled with a second talc 94b, a bolting portion 96 for mounting is attached to the distal end of the housing 13, an airtight ring 98 is fit between the bolting portion 96 and the housing 13, and a caulking rubber plug 100 is fixed to the rear end of the housing 13. By using such a structure, the sensor element 12 can be fixed and airtight-packaged in the housing 13. A lead wire 102 is introduced from an external electric circuit through the rubber plug 100 and electrically connected to the connector 88 in the housing 13. The sensor element 12 is fixed by the first and second talcs 94a, 94b by pressing a talc powder using the first to third supporting members 86a to 86c.

As shown in FIG. 3, four edges of the solid electrolyte body 11 are chamfered over the entire length of the solid electrolyte body 11 of the gas sensor 10. Thus, first to fourth chamfered portions 104a to 104d are formed on the four edges. In this case, even when the sensor element 12 is exposed to the measurement gas such as an exhaust gas with a high temperature or when the sensor element 12 is maintained at a high temperature by a heater installed therein, the thermal stress concentration in the solid electrolyte body 11 can be relaxed to improve the thermal shock resistance.

Figure 4A:
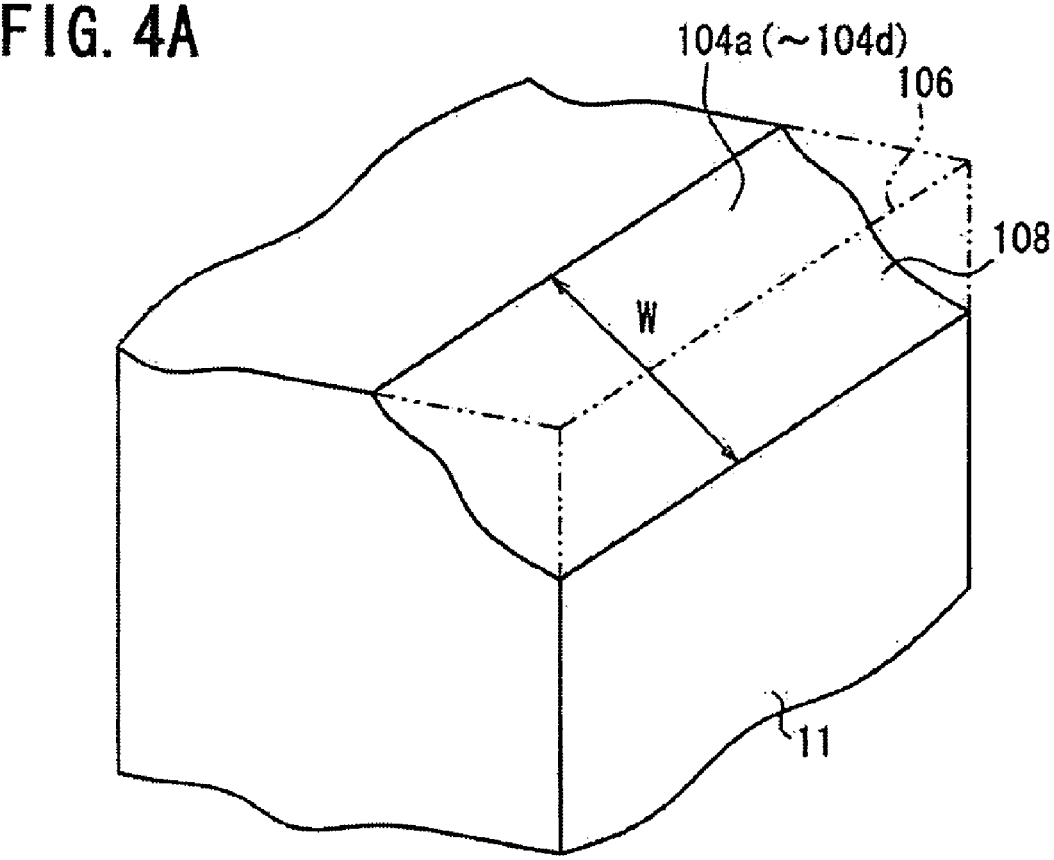
FIGS. 4A and 4B are views for explaining width of chamfered portions.
Figure 4B:
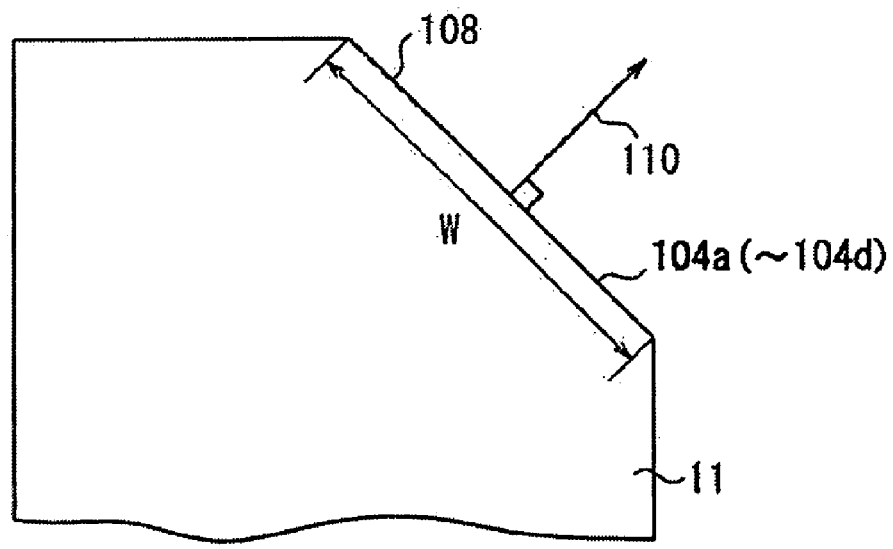

The widths W of the first to fourth chamfered portions 104a to 104d are within a range of 30 to 240 μm. As shown in FIGS. 4A and 4B, the width W of each of the first to fourth chamfered portions 104a to 104d means the length of a C surface (flat surface) 108 in the direction perpendicular to a normal line 110 (see FIG. 4B). The flat surface is formed in the chamfering process by cutting the corner of an edge portion 106 represented by an imaginary line (a two-dot chain line).

Figure 5A:
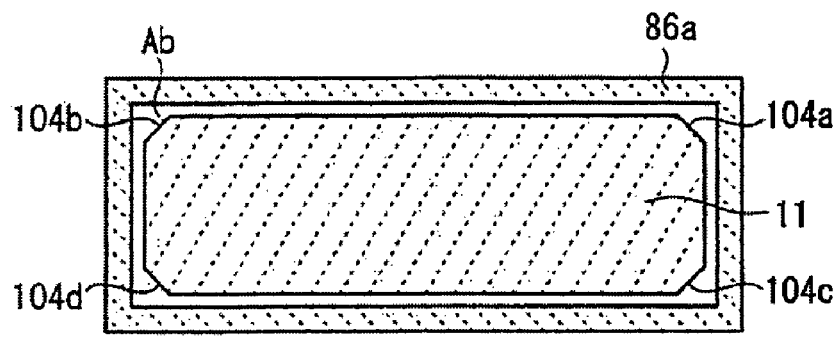
FIG. 5A is a cross-sectional view for explaining a first space area.
Figure 5B:
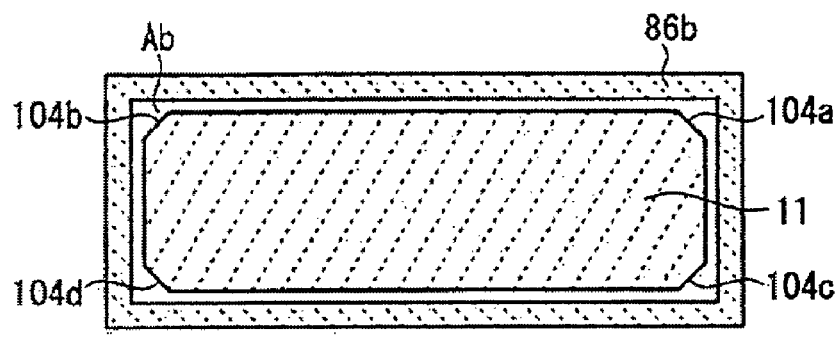
FIG. 5B is a cross-sectional view for explaining a second space area.
Figure 5C:
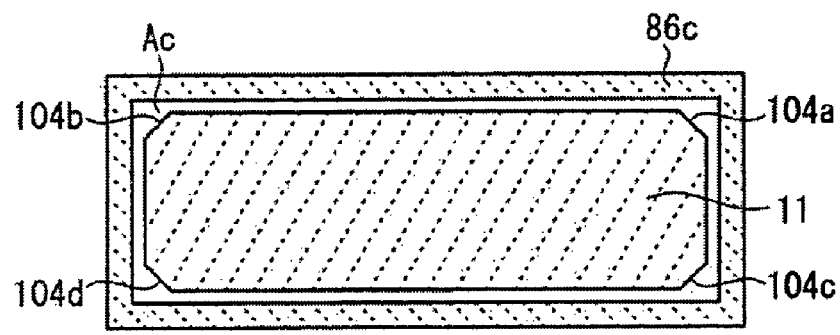
FIG. 5C is a cross-sectional view for explaining a third space area.

In this gas sensor 10, as shown in FIG. 5A, when Aa represents the cross-sectional area of a space formed between the first supporting member 86a and the portion in the solid electrolyte body 11 corresponding to the first supporting member 86a (the first space area), as shown in FIG. 5B, Ab represents the cross-sectional area of a space formed between the second supporting member 86b and the portion in the solid electrolyte body 11 corresponding to the second supporting member 86b (the second space area) and as shown in FIG. 5C, Ac represents the cross-sectional area of a space formed between the third supporting member 86c and the portion in the solid electrolyte body 11 corresponding to the third supporting member 86c (the third space area), the first space area Aa, the second space area Ab, and the third space area Ac are within a range of 1.5 to 3.0 mm$^2$.

Figure 5D:
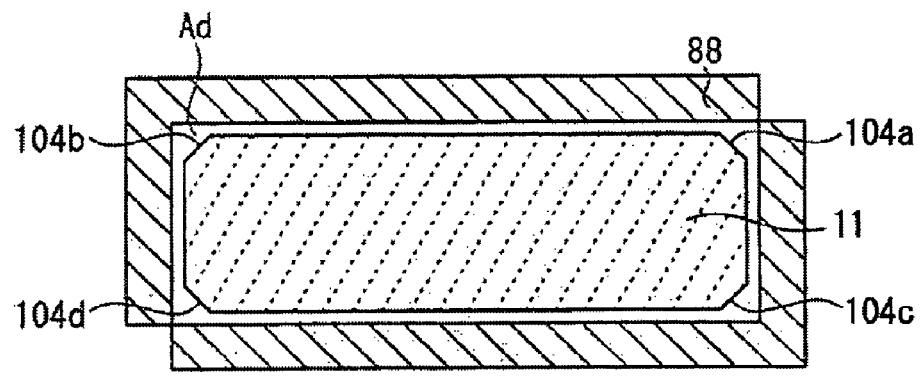
FIG. 5D is a cross-sectional view for explaining a fourth space area.

Further, in this embodiment, as shown in FIG. 5D, when Ad represents the cross-sectional area of a space formed between the connector 88 and the portion in the solid electrolyte body 11 corresponding to the connector 88 (the fourth space area), the fourth space area Ad is within a range of 1.5 to 3.0 mm$^2$.

By controlling the widths of the first to fourth chamfered portions 104a to 104d in the solid electrolyte body 11 within the above range, the sensor element 12 can be prevented from the breakage by contact with the housing 13 (e.g. contact of the solid electrolyte body 11 with the first to third supporting members 86a to 86c or the connector 88) in practical use in an internal combustion engine or the like, to improve the reliability of the gas sensor 10.

In the gas sensor 10 of the embodiment, the solid electrolyte body 11 can be easily formed by cutting off the four edges over the entire length, so that the production thereof can be simplified to reduce the production costs.

Two producing methods (first and second producing methods) according to this embodiment will be described below with reference to FIGS. 6 to 16C.

As shown in FIGS. 6 and 7, in the first producing method, a guide plate 114 has a through-hole 112 into which an edge portion 106 of the solid electrolyte body 11 is inserted, a press jig 116 is placed such that the press jig 116 faces one major surface 114a of the guide plate 114, the solid electrolyte body 11 is placed on and fixed to the upper surface of the press jig 116, and a cutter 118 is slid along the other major surface 114b of the guide plate 114. The press jig 116 has an upper plate 120 which the solid electrolyte body 11 is placed on and fixed to, and a transfer mechanism 122 for moving the upper plate 120.

By using the transfer mechanism 122, the upper plate 120 can be moved closer to or away from the major surface 114a of the guide plate 114, and can be rotated around a center line 124 of the upper plate 120, extending along the longitudinal direction.

Figure 8A:
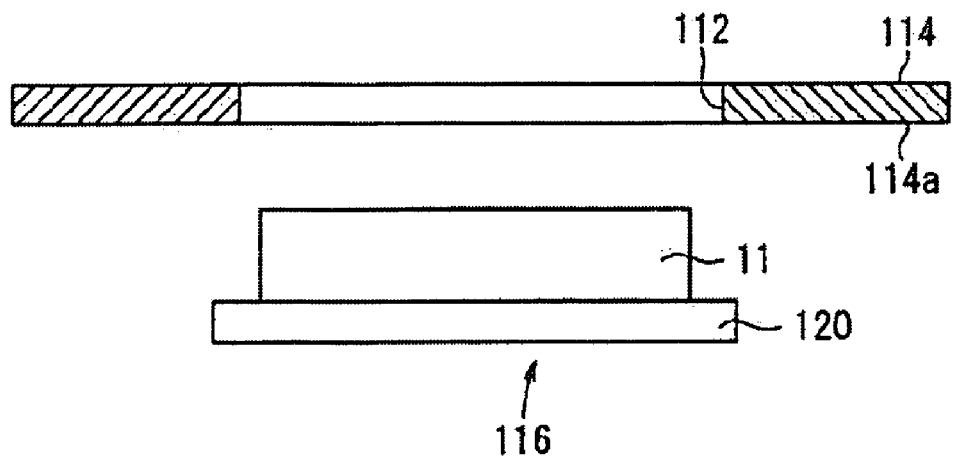
FIG. 8A is a view showing the step of placing and fixing the solid electrolyte body onto the upper plate.

In the first producing method, as shown in FIG. 8A, the solid electrolyte body 11 is placed on and fixed to the upper plate 120 of the press jig 116 such that one major surface (e.g. an upper surface) of the solid electrolyte body 11 faces the major surface 114a having the through-hole 112 of the guide plate 114.

Figure 8B:
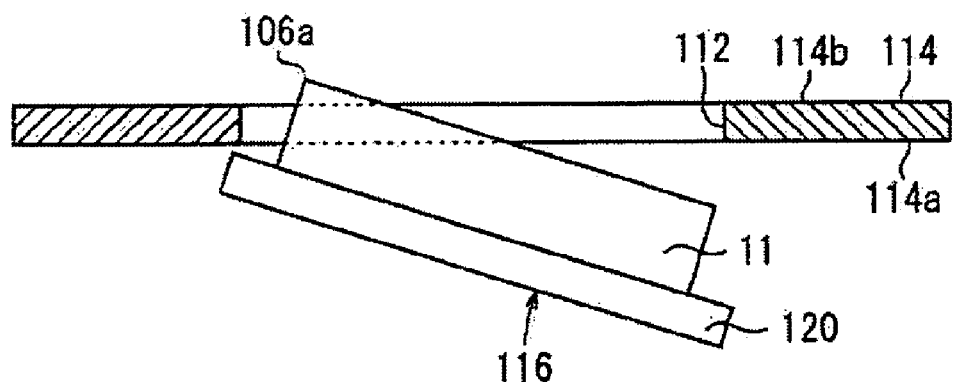
FIG. 8B is a view showing the step of inserting a first edge portion of the solid electrolyte body into a through-hole of the guide plate.

As shown in FIG. 8B, by using the transfer mechanism 122, the upper plate 120 is rotated to incline the solid electrolyte body 11 in one direction, and the solid electrolyte body 11 is moved toward the other major surface 114b of the guide plate 114, so that a first edge portion 106a of the solid electrolyte body 11 protrudes from the through-hole 112.

Figure 8C:
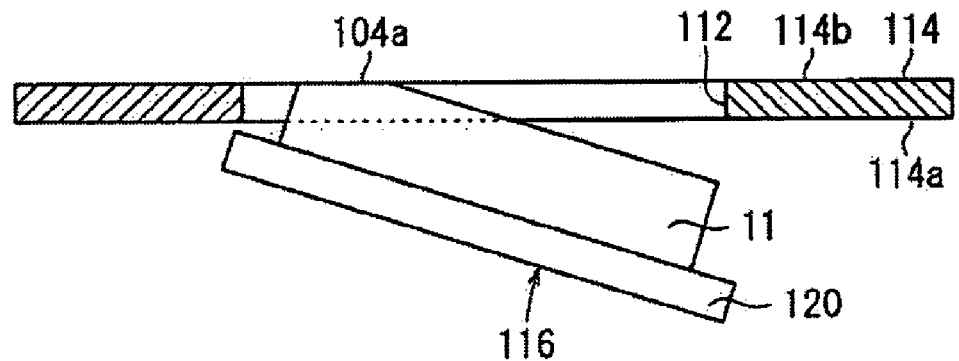
FIG. 8C is a view showing the step of chamfering the first edge portion.

As shown in FIG. 8C, the cutter 118 is slid along the other major surface 114b of the guide plate 114 (see FIG. 7), whereby the first edge portion 106a is chamfered to form a first chamfered portion 104a.

In the step of FIG. 8B, the angle of the rotation of the upper plate 120 (the angle of the inclination of the solid electrolyte body 11) or the extent of the movement of the upper plate 120 toward the guide plate 114 is preferably controlled such that the first chamfered portion 104a to be formed in the next step of FIG. 8C has a width of 30 to 240 µm.

Figure 9A:
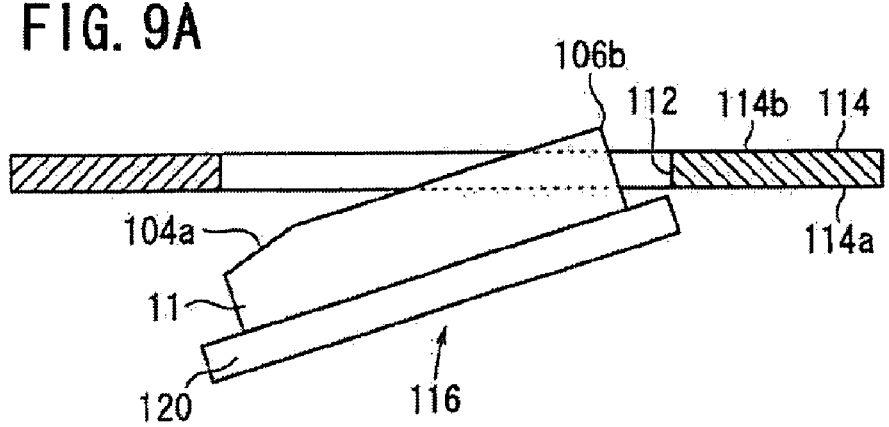
FIG. 9A is a view showing the step of inserting a second edge portion of the solid electrolyte body into the through-hole of the guide plate.

Then, as shown in FIG. 9A, by using the transfer mechanism 122, the upper plate 120 is rotated to incline the solid electrolyte body 11 in the opposite direction, and the solid electrolyte body 11 is moved toward the other major surface 114b of the guide plate 114, so that a second edge portion 106b of the solid electrolyte body 11 protrudes from the through-hole 112.

Figure 9B:
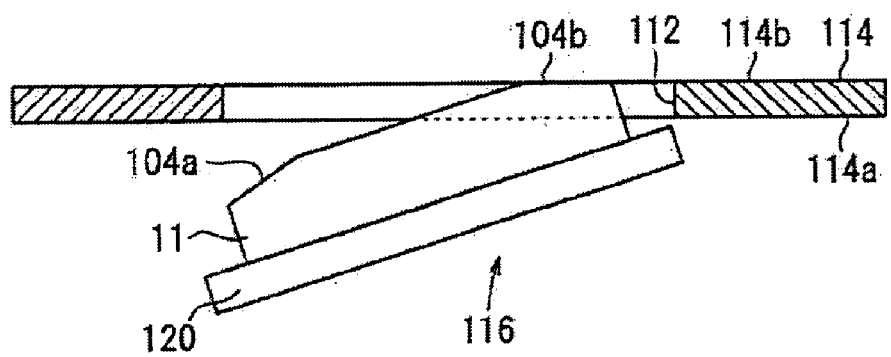
FIG. 9B is a view showing the step of chamfering the second edge portion.

As shown in FIG. 9B, the cutter 118 is slid along the other major surface 114b of the guide plate 114, whereby the second edge portion 106b is chamfered to form a second chamfered portion 104b.

Also in the step of FIG. 9A, the angle of the rotation of the upper plate 120 (the angle of the inclination of the solid electrolyte body 11) or the extent of the movement of the upper plate 120 toward the guide plate 114 is preferably controlled such that the second chamfered portion 104b to be formed in the next step of FIG. 9B has a width of 30 to 240 µm.

Figure 9C:
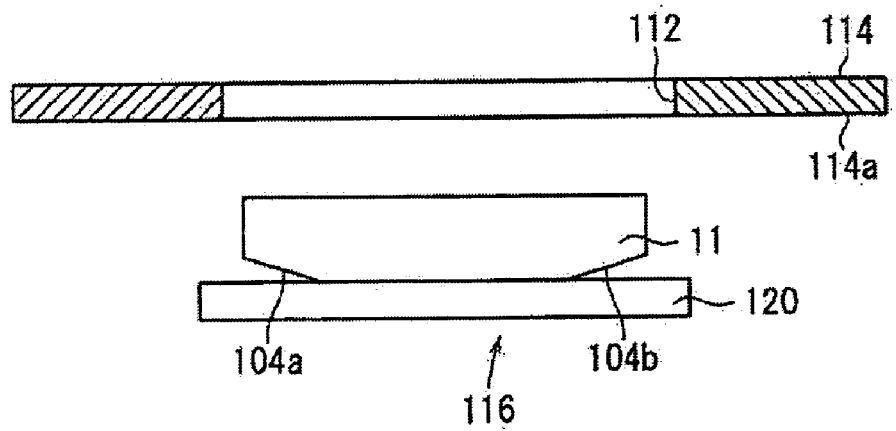
FIG. 9C is a view showing the step of resetting the solid electrolyte body on the upper plate.

As shown in FIG. 9C, the solid electrolyte body 11 is then placed on and fixed to the upper plate 120 such that the other major surface (e.g. a lower surface) of the solid electrolyte body 11 faces the major surface 114a of the guide plate 114.

Figure 10A:
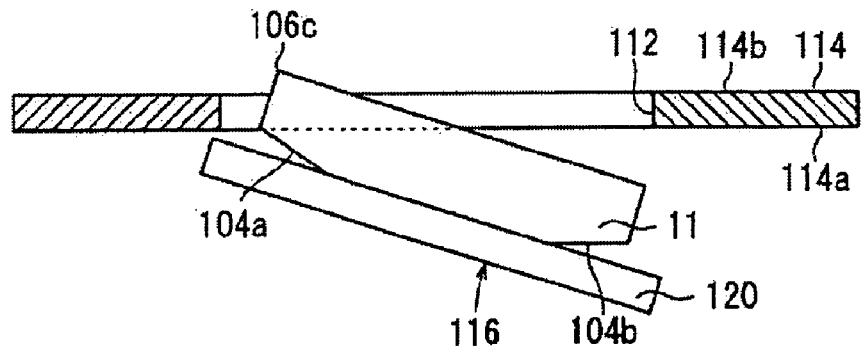
FIG. 10A is a view showing the step of inserting a third edge portion of the solid electrolyte body into the through-hole of the guide plate.

Then, as shown in FIG. 10A, by using the transfer mechanism 122, the upper plate 120 is rotated to incline the solid electrolyte body 11 in one direction, and the solid electrolyte body 11 is moved toward the other major surface 114b of the guide plate 114, so that a third edge portion 106c of the solid electrolyte body 11 protrudes from the through-hole 112.

Figure 10B:
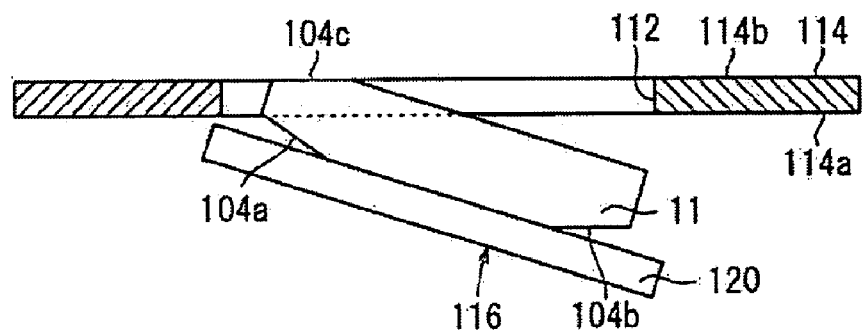
FIG. 10B is a view showing the step of chamfering the third edge portion.

As shown in FIG. 10B, the cutter 118 is slid along the other major surface 114b of the guide plate 114, whereby the third edge portion 106c is chamfered to form a third chamfered portion 104c.

Figure 10C:
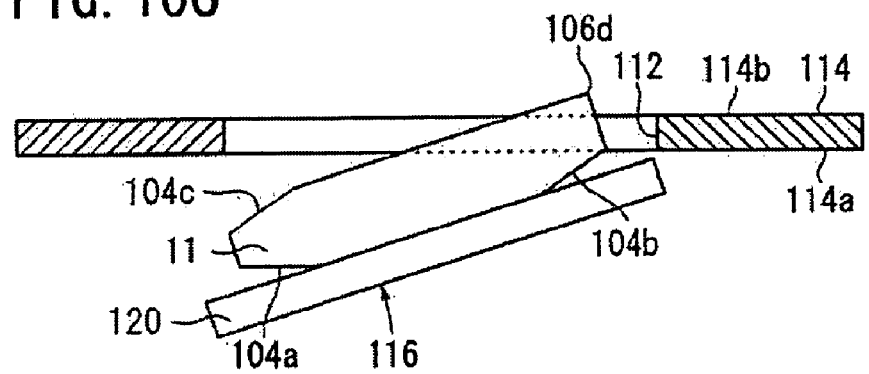
FIG. 10C is a view showing the step of inserting a fourth edge portion of the solid electrolyte body into the through-hole of the guide plate.

As shown in FIG. 10C, by using the transfer mechanism 122, the upper plate 120 is rotated to incline the solid electrolyte body 11 in the opposite direction, and the solid electrolyte body 11 is moved toward the other major surface 114b of the guide plate 114, so that a fourth edge portion 106d of the solid electrolyte body 11 protrudes from the through-hole 112.

Figure 10D:
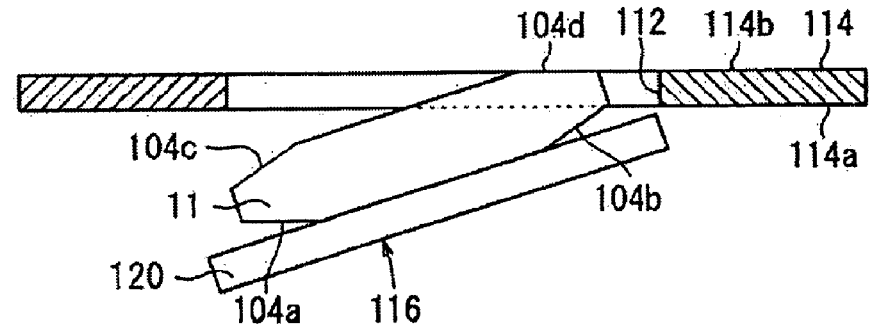
FIG. 10D is a view showing the step of chamfering the fourth edge portion.
Figure 12:
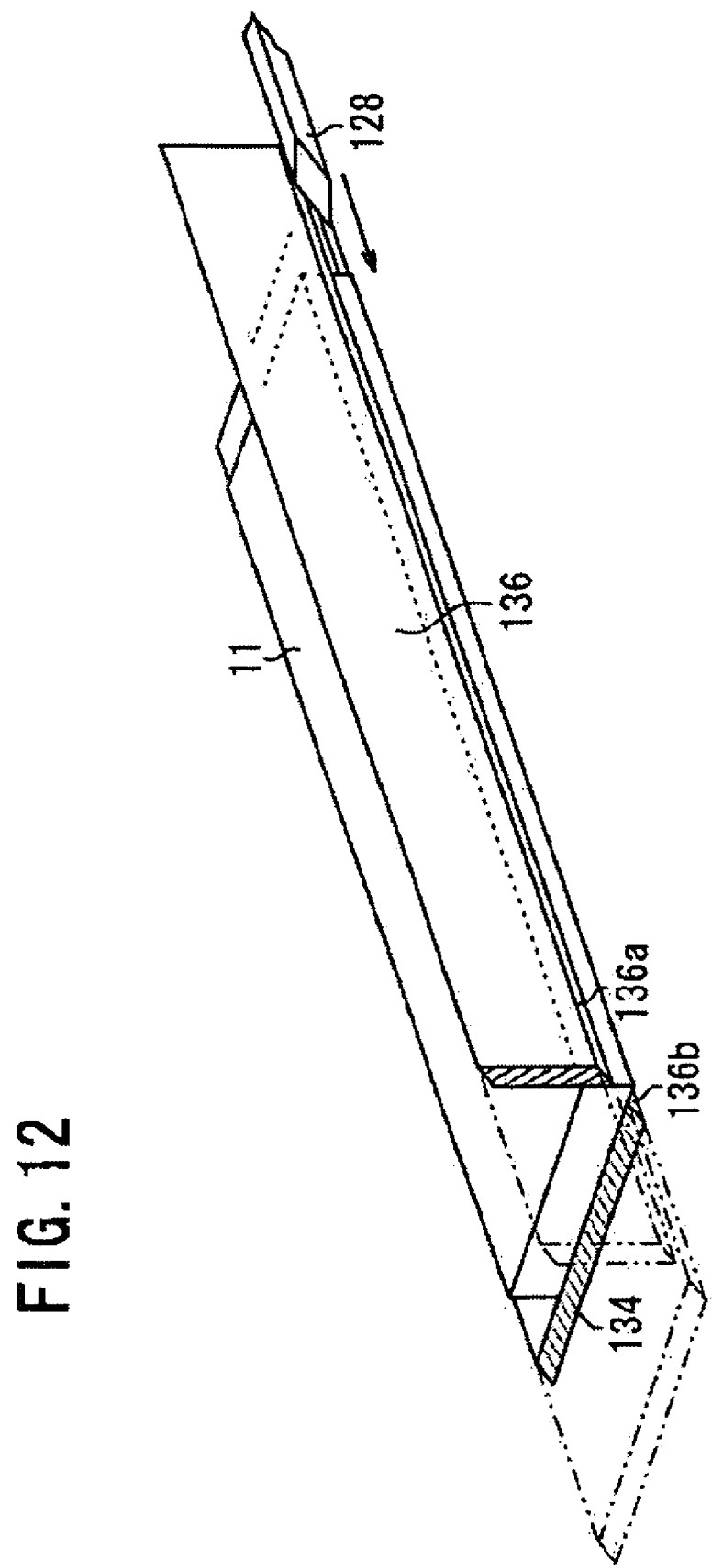
FIG. 12 is a perspective view showing the apparatus for the second producing method, particularly first and second plates to which a solid electrolyte body is pressed, and a cutter.

As shown in FIG. 10D, the cutter 118 is slid along the other major surface 114b of the guide plate 114, whereby the fourth edge portion 106d is chamfered to form a fourth chamfered portion 104d.

Also in the steps of FIGS. 10A and 10C, the angle of the rotation of the upper plate 120 (the angle of the inclination of the solid electrolyte body 11) or the extent of the movement of the upper plate 120 toward the guide plate 114 is preferably controlled such that the third and fourth chamfered portions 104c, 104d have a width of 30 to 240 µm.

It is preferred that the cutter 118 and the solid electrolyte body 11 are heated respectively to raise the temperature of the solid electrolyte body 11 to the Tg (the glass transition point) or higher in the chamfering process. In this case, the solid electrolyte body 11 is softened, and the resultant chamfer surface has no defects such as fraying.

The second producing method will be described below with reference to FIGS. 11 to 16C.

As shown in FIG. 11, a positioning jig 126, a cutter 128 (see FIG. 12), a first press jig 130, and a second press jig 132 are used in the second producing method. The positioning jig 126 has a first plate 134, a second plate 136 nonparallel to the first plate 134, and a space 138 (see FIG. 13A) formed between the first and second plates 134, 136. An end surface 134a of the first plate 134 is located in the vicinity of an end surface 136a of the second plate 136. The end surface 134a of the first plate 134, the space 138, and the end surface 136a of the second plate 136 forms one surface 140 (represented by the dashed line), and the cutter 128 (see FIG. 12) is slid in the longitudinal direction along the surface 140. The solid electrolyte body 11 placed on the first plate 134 is pressed by the first press jig 130 toward the first plate 134, and is pressed by the second press jig 132 toward the second plate 136.

The positioning jig 126 has an adjustment unit 142 for controlling the width Da of the space 138. The adjustment unit 142 contains a first transfer mechanism 144 for horizontally moving the first plate 134 and a second transfer mechanism 146 for vertically moving the second plate 136. By using the adjustment unit 142, the transfer of the first and second plates 134 and 136 is controlled such that the single surface 140 is formed by the end surface 134a of the first plate 134, the space 138, and the end surface 136a of the second plate 136.

Figure 13A:
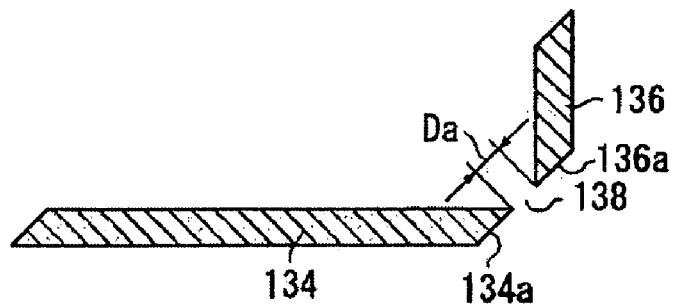
FIG. 13A is a view showing the step of controlling the width of the space between the first and second plates.

In the second producing method, as shown in FIG. 13A, the width Da of the space 138 between the first and second plates 134 and 136 is controlled.

Figure 13B:
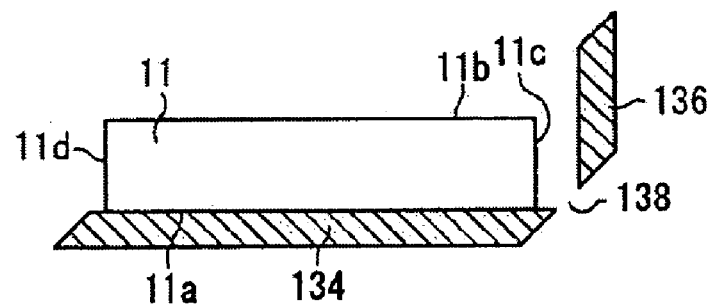
FIG. 13B is a view showing the step of placing the solid electrolyte body on the first plate.

As shown in FIG. 13B, the solid electrolyte body 11 is placed on the first plate 134 such that one major surface (e.g. an upper surface 11a) of the solid electrolyte body 11 faces the first plate 134.

Figure 13C:
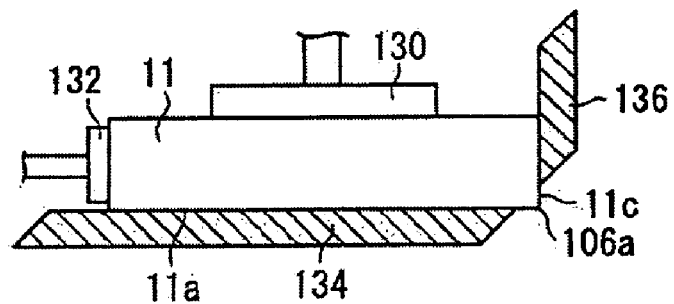
FIG. 13C is a view showing the step of inserting a first edge portion of the solid electrolyte body into the space.

As shown in FIG. 13C, the solid electrolyte body 11 is pressed by the first press jig 130 toward the first plate 134, and is pressed by the second press jig 132 toward the second plate 136 to bring a first side surface 11c of the solid electrolyte body 11 into contact with the second plate 136. As a result, a first edge portion 106a of the solid electrolyte body 11 protrudes from the space 138.

Figure 13D:
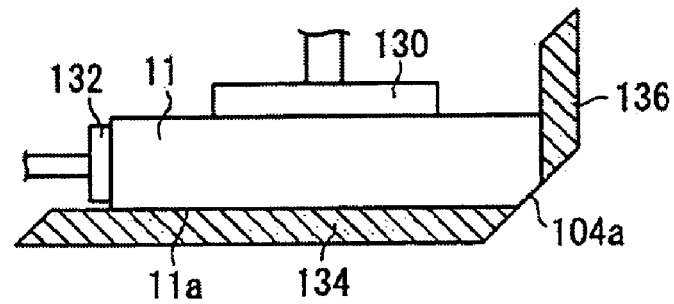
FIG. 13D is a view showing the step of chamfering the first edge portion.

As shown in FIG. 13D, the cutter 128 is slid in the longitudinal direction of the first edge portion 106a protruding from the space 138, whereby the first edge portion 106a is chamfered to form a first chamfered portion 104a.

Figure 14A:
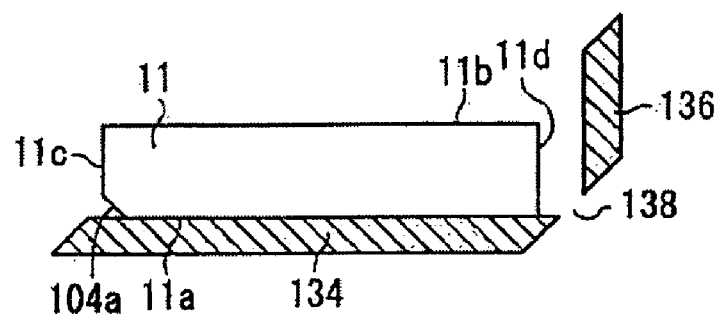
FIG. 14A is a view showing the step of resetting the solid electrolyte body on the first plate.

Then, for example, as shown in FIG. 14A, the solid electrolyte body 11 is placed on the first plate 134 such that the upper surface 11a of the solid electrolyte body 11 faces the first plate 134, and a second side surface 11d of the solid electrolyte body 11 (a side surface on the side opposite to the first side surface 11c) faces the second plate 136.

Figure 14B:
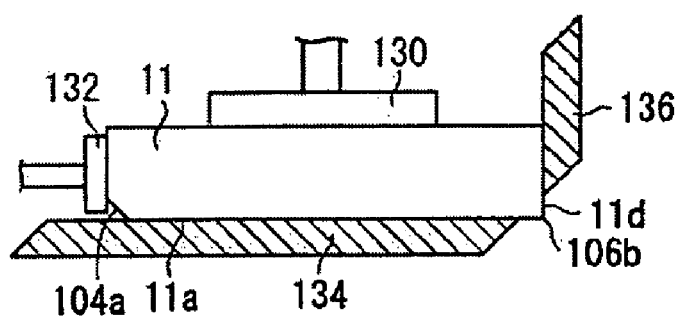
FIG. 14B is a view showing the step of inserting a second edge portion of the solid electrolyte body into the space.

As shown in FIG. 14B, the solid electrolyte body 11 is pressed by the first press jig 130 toward the first plate 134, and is pressed by the second press jig 132 toward the second plate 136 to bring the second side surface 11d of the solid electrolyte body 11 into contact with the second plate 136. As a result, a second edge portion 106b of the solid electrolyte body 11 protrudes from the space 138.

Figure 14C:
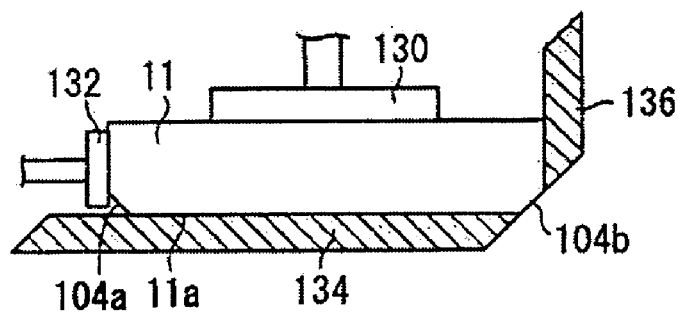
FIG. 14C is a view showing the step of chamfering the second edge portion.

As shown in FIG. 14C, the cutter 128 is slid in the longitudinal direction of the second edge portion 106b protruding from the space 138, whereby the second edge portion 106b is chamfered to form a second chamfered portion 104b.

Figure 15A:
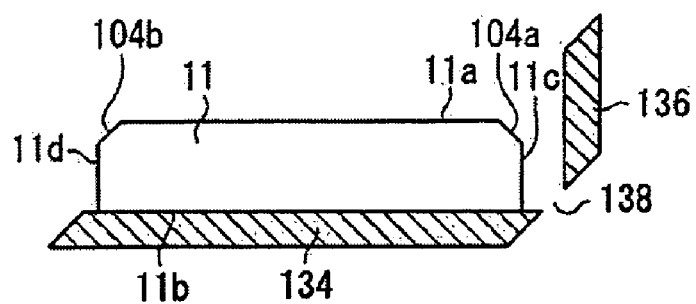
FIG. 15A is a view showing the step of resetting the solid electrolyte body on the first plate.

Then, for example, as shown in FIG. 15A, the solid electrolyte body 11 is placed on the first plate 134 such that a lower surface 11b of the solid electrolyte body 11 faces the first plate 134, and the first side surface 11c of the solid electrolyte body 11 faces the second plate 136.

Figure 15B:
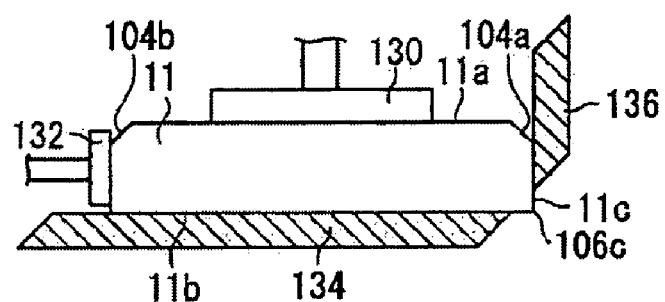
FIG. 15B is a view showing the step of inserting a third edge portion of the solid electrolyte body into the space.

As shown in FIG. 15B, the solid electrolyte body 11 is pressed by the first press jig 130 toward the first plate 134, and is pressed by the second press jig 132 toward the second plate 136 to bring the first side surface 11c of the solid electrolyte body 11 into contact with the second plate 136. As a result, a third edge portion 106c of the solid electrolyte body 11 protrudes from the space 138.

Figure 15C:
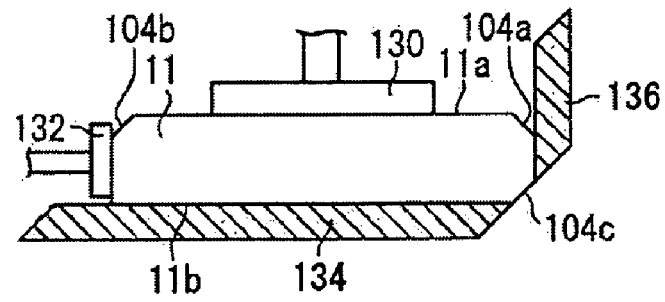
FIG. 15C is a view showing the step of chamfering the third edge portion.

As shown in FIG. 15C, the cutter 128 is slid in the longitudinal direction of the third edge portion 106c protruding from the space 138, whereby the third edge portion 106c is chamfered to form a third chamfered portion 104c.

Figure 16A:
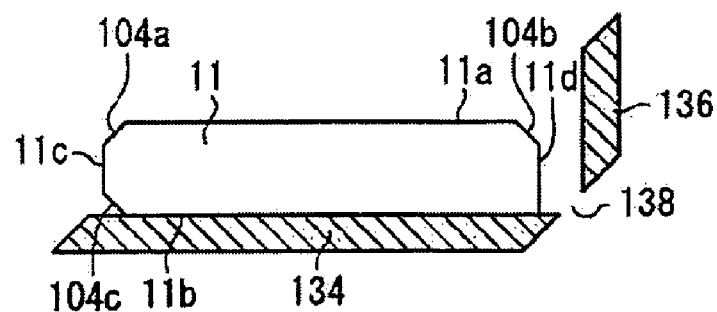
FIG. 16A is a view showing the step of resetting the solid electrolyte body on the first plate.

Then, as shown in FIG. 16A, the solid electrolyte body 11 is placed on the first plate 134 such that the lower surface 11b of the solid electrolyte body 11 faces the first plate 134, and the second side surface 11d of the solid electrolyte body 11 faces the second plate 136.

Figure 16B:
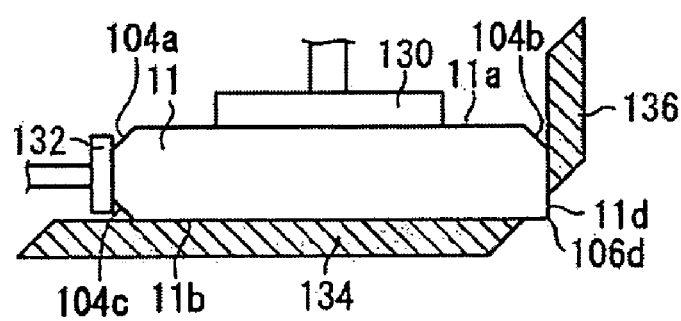
FIG. 16B is a view showing the step of inserting a fourth edge portion of the solid electrolyte body into the space.

As shown in FIG. 16B, the solid electrolyte body 11 is pressed by the first press jig 130 toward the first plate 134, and is pressed by the second press jig 132 toward the second plate 136 to bring the second side surface 11d of the solid electrolyte body 11 into contact with the second plate 136. As a result, a fourth edge portion 106d of the solid electrolyte body 11 protrudes from the space 138.

Figure 16C:
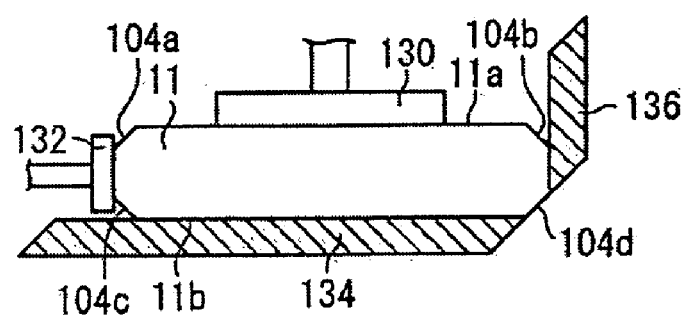
FIG. 16C is a view showing the step of chamfering the fourth edge portion.

As shown in FIG. 16C, the cutter 128 is slid in the longitudinal direction of the fourth edge portion 106d protruding from the space 138, whereby the fourth edge portion 106d is chamfered to form a fourth chamfered portion 104d.

In the step of FIG. 13A, the width Da of the space 138 between the first and second plates 134 and 136 is preferably controlled by the adjustment unit 142 such that each of the first to fourth chamfered portions 104a to 104d to be formed in the following steps of FIGS. 13D, 14C, 15C, and 16C has a width W of 30 to 240 μm.

Also in the second producing method, it is preferred that the cutter 128 and the solid electrolyte body 11 are heated respectively to raise the temperature of the solid electrolyte body 11 to the Tg (the glass transition point) or higher in the chamfering process. In this case, the solid electrolyte body 11 is softened, and the resultant chamfer surface has no defects such as fraying.

As described above, according to the first and second methods of the present invention, the oxygen sensor of Japanese Patent No. 2786507 designed for improving thermal shock resistance can be further improved, and a more reliable gas sensor capable of showing a higher thermal shock resistance and being prevented from the breakage by contact with the supporting member of the housing, etc. can be easily produced.

It is a matter of course that the method of the present invention for producing a gas sensor is not limited to the embodiment described above, which may be embodied in other various forms without deviating from the gist or essential characteristics of the present invention.

The invention claimed is:

1. A method for producing a gas sensor comprising a sensor element for detecting a concentration of a specific gas component in a measurement gas, said sensor element having a rectangular solid structure of a solid electrolyte body containing a ceramic material, said method comprising:

using a positioning jig that includes a first plate, a second plate nonparallel to said first plate, and a space formed between said first plate and said second plate, an end surface of said first plate being located in the vicinity of an end surface of said second plate;

using first and second press jig mechanisms to clamp said solid electrolyte body against said first and second plates, respectively, such that a major surface of said solid electrolyte body is in contact with said first plate, a side surface thereof is in contact with said second plate, and an edge between said major surface and said side surface protrudes from said space; and holding said solid electrolyte body stationary while sliding a heated cutter in the longitudinal direction of said edge protruding from said space to chamfer said edge, wherein said solid electrolyte body is heated at least to the glass transition point temperature of the ceramic material prior to chamfering said edge.

2. The method according to claim 1, wherein said end surface of said first plate, said space, and said end surface of said second plate form a surface in said positioning jig, and said cutter is slid along said surface to chamfer said edge.

3. The method according to claim 1, wherein said clamping of said electrolyte body against said first and second plates and said chamfering of said edge are carried out repeatedly to consequently chamfer four edges of said solid electrolyte body.

\* \* \* \* \*